United States Patent [19]

Chow et al.

[11] Patent Number: 5,145,668
[45] Date of Patent: Sep. 8, 1992

[54] FLUORIDE CONTAINING MOUTH RINSES, DENTIFRICES, AND GELS

[75] Inventors: Laurence C. Chow, Germantown; Shozo Takagi, Gaithersburg, both of Md.

[73] Assignee: American Dental Association Health Foundation, Chicago, Ill.

[21] Appl. No.: 633,628

[22] Filed: Dec. 21, 1990

Related U.S. Application Data

[63] Continuation-in-part of Ser. No. 322,700, Mar. 3, 1989, abandoned.

[51] Int. Cl.$^5$ .................. A61K 7/18; A61K 33/16
[52] U.S. Cl. ........................ 424/52; 424/673; 424/674
[58] Field of Search .................. 424/52, 673–676

[56] References Cited

U.S. PATENT DOCUMENTS

| | | | |
|---|---|---|---|
| 4,048,300 | 9/1977 | Tomlinson et al. | 424/52 |
| 4,080,440 | 3/1978 | DiGiulio et al. | 424/52 |
| 4,083,955 | 4/1978 | Grabenstetter et al. | 424/52 |
| 4,108,980 | 8/1978 | Duff | 424/52 |
| 4,177,258 | 12/1979 | Gaffar et al. | 424/52 |
| 4,183,915 | 1/1980 | Gaffar et al. | 424/52 |
| 4,348,381 | 9/1982 | Gaffar et al. | 424/52 |
| 4,397,837 | 8/1983 | Raaf et al. | 424/52 |
| 4,460,565 | 7/1984 | Westrate et al. | 424/52 |
| 4,532,124 | 7/1985 | Pearce | 424/52 |
| 4,556,561 | 12/1985 | Brown et al. | 424/52 |
| 4,861,590 | 8/1989 | Grodberg | 424/602 |

*Primary Examiner*—Shep K. Rose
*Attorney, Agent, or Firm*—Allegretti & Witcoff, Ltd.

[57] ABSTRACT

Previous mouthwashes and dentifrices containing fluoride contributed relatively modest amounts of additional fluoride to the tooth surfaces, and scavenged calcium from the teeth. The present invention can deposit significantly more fluoride in the mouth than previously used formulations containing comparable amounts of fluoride, without scavenging calcium from the teeth. The invention includes a method of fluoridating teeth comprising (1) mixing in an aqueous environment a first component comprising a stable, non-toxic soluble calcium salt with a second component comprising a stable, non-toxic readily hydrolyzable complex fluoride compound, resulting in hydrolysis of the fluoride compound and precipitation of calcium fluoride, followed by (2) prompt application of the mixture to tooth surfaces. The invention also contemplates mouth rinses, denifrices, gels or pastes, and chewable tablets for application of the above-described compositions.

7 Claims, No Drawings

FLUORIDE CONTAINING MOUTH RINSES, DENTIFRICES, AND GELS

This application is a continuation-in-part of application Ser. No. 07/322,700, filed on Mar. 3, 1989, now abandoned.

BACKGROUND OF THE INVENTION

This invention was supported in part by research grant number DE05354 to the American Dental Association Health Foundation from the National Institute of Dental Research. The Government has certain rights in this invention.

Self-applied fluorides in the forms of mouth rinses and dentifrices are widely used in this country and elsewhere in the world. They have been shown to be effective in reducing tooth decay. The fluoride containing mouth rinses formulated for daily use usually contain 250 parts per million (ppm) of fluoride as sodium fluoride or stannous fluoride. The fluoride dentifrices typically contain 1000 ppm of fluoride as sodium fluoride or sodium monofluorophosphate. The cariostatic effects of both of these fluoride regimens are believed to derive from their ability to deposit fluoride on the surfaces of teeth and other tissues in the mouth. Although the deposited fluoride is labile in nature and is easily leached out of teeth and mouth tissues, the daily application of either the rinse or dentifrice can produce and maintain an elevated level of fluoride in the mouth.

U.S. Pat. No. 4,556,561 discloses solutions, gels, and substantially nonaqueous dispersions that form dicalcium phosphate dihydrate under appropriate conditions, as well as methods for their use. These compositions are useful in topically fluoridating and/or mineralizing dental tissue, such as enamel, dentin, and exposed root surfaces. The incorporated fluoride is in the form of $Ca_5(PO_4)_3F$ and is more permanently retained than $CaF_2$ and other fluoridation products.

U.S. Pat. No. 4,048,300 discloses a single dental preparation including a material containing calcium and phosphorous. The calcium/phosphorous containing component may also include fluoride. Examples of calcium/phosphorous/fluoride components include fluorapatite, fluorohydroxy apatite, apatite, calcium deficient apatite, and hydroxy apatite substituted by a fluoranion. This component is useful in a dental cream.

U.S. Pat. No. 4,080,440 discloses a method for the remineralization of tooth enamel using a two solution system. The first solution is a cationic solution containing a calcium salt and optionally a heavy metal cation. The second solution is an anionic solution containing a phosphate salt and optionally non-phosphatic anions including fluoride ions. The pH of the solutions ranges from 2 to 4 and the ratio of calcium to phosphorous ranges from 0.01 to 100. The solution, produced by mixing the two-components, is described as a "metastable" solution and requires a residence time in the mouth of from 10 seconds to about 3 minutes in order to raise the pH of the solution such that the components of the solution precipitate in the tooth resulting in enamel remineralization.

U.S. Pat. No. 4,803,955 describes a two-step process for remineralizing dental enamel. In the process, two solutions, one comprising a calcium salt, and the other solution comprising a phosphorous salt along with an optional fluoride salt, are sequentially contacted with dental enamel. The sequential solution contact results in the surface of the enamel being remineralized.

U.S. Pat. No. 4,108,980 describes a process for applying fluoride to teeth with a material having calcium and phosphate components. The dental material includes a salt which ionizes to produce fluoride ions. The formulations described in this invention are made well in advance of application to tooth surfaces.

U.S. Pat. No. 4,177,258 and 4,183,915 describe stable solutions for dental remineralization. The solutions include a source of calcium ions, a source of phosphate ions and a source of fluoride. The solutions also include an anti-nucleating agent consisting of diamine tetramethylenephosphonic acids having a specific formula. The anti-nucleating agent stabilizes the calcium ions and phosphorous ions and prevents them from precipitating as large, insoluble apatite crystals.

U.S. Pat. No. 4,348,381 describes solutions similar to those described in the '258 and '915 patents above. However, the anti-nucleating agent of the '381 solution is PBTA and its water soluble salts.

U.S. Pat. No. 4,397,837 describes a two-phase dental composition in which the two phases are combined when applied to teeth. The first phase of the composition includes a calcium component. The second phase includes a water soluble phosphate component and a water soluble fluoride component.

U.S. Pat. No. 4,460,565 describes a remineralizing dentrifice composition. The composition includes a calcium containing component, two fluoride components, an alkali or alkaline earth metal fluoride and an alkali metal fluorophosphate, two phosphate components, a soluble cyclic alkali metal phosphate and a soluble linear phosphate.

U.S. Pat. No. 4,532,124 describes a dental rinse. The dental rinse includes water soluble salts of fluorine, calcium and phosphorous. The composition additionally includes substance metabolized into an alkali, such as urea, which raises the solution pH causing calcium precipitation.

U.S. Pat. Nos. 4,606,912 and 4,610,873 describe a clear, stable aqueous mouthwash free of calcium phosphate crystals. The mouthwash includes a chelating agent in combination with a calcium ion source, and a phosphate ion source. The calcium ion source consists of a component capable of providing fluoride ions. The aqueous composition contains calcium ions, phosphate ions, and fluoride ions.

U.S. Pat. No. 4,714,608 describes an aqueous dental preparation. The dental preparation includes a fluoride component in a solution having a pH less than 2. The compound can be applied to teeth either before or after the teeth are treated with calcium. This provides for the precipitation of $CaF_2$ as a thin homogeneous layer on the tooth enamel.

U.S. Pat. No. 4,861,590 describes a sustained release fluoride in calcium composition. The composition includes MFP(monofluoraphosphate) and an ionizable calcium source. Sodium fluoride may be added to the composition as desired.

SUMMARY OF THE INVENTION

A constant-composition titration (CCT) technique, recently developed in our laboratory, makes it possible to measure quantitatively the minute amount of fluoride deposited on the tooth surface from a single application of fluoride containing rinse or dentifrice in vitro. By using this CCT technique (reported at Sieck, Takagi and Chow 67 J. Dent. Res. (Special Issue) Abstract 2211 (Mar. 1988)), we were able to determine that a 1-minute rinse with a 250 ppm fluoride rinse deposited 0.34 micro grams/cm$^2$ of F, and a 1-minute brushing with a 1000 ppm fluoride containing dentifrice deposited 0.25 micro grams/cm$^2$ of fluoride on the tooth surface. Based on the recommended quantity for the rinse (10 mL) or for the dentifrice (1 gram) per application and the total surface area of the teeth in the mouth, it is estimated that less than 0.5% of the fluoride in the rinse or the dentifrice is deposited on the teeth. Some of the fluoride is also deposited in the plaque and soft tissue surfaces, but the bulk of the fluoride contained in the rinses or dentifrices is presumably expectorated (a small fraction of fluoride is also swallowed).

A major reason for this very low yield of fluoride retention is the lack of a reaction mechanism for the fluoride in the rinse or dentifrice to precipitate out during the short application time.

In contrast to the above formulations, the present invention discloses solutions, gels, dentifrices, and chewable tablets that are useful for depositing CaF$_2$ onto the surfaces of teeth and other oral tissues. These formulations are significantly more efficacious than currently used agents containing comparable amounts of fluoride for two reasons: (1) the inventive formulations can deposit up to 15 times more fluoride, and (2) the inventive formulations do not cause any loss of tooth mineral even with frequent and protracted use.

The present invention involves a two-component system. One component contains a soluble calcium salt, and the other a complex fluoride compound. When the two-components are brought in contact just prior to application to the teeth, a rapid but controlled reaction precipitates extremely fine particles of calcium fluoride continuously within the application period. The inventive system, when used in the form of mouth rinses, dentifrices, gels, or chewable tablets, can deposit significantly more fluoride in the mouth than presently used formulations containing comparable amounts of fluoride. Thus, the new formulations based on this two-component system should be significantly more efficacious than those currently in use.

Also, since none of the currently used fluoride agents contains soluble calcium in the formulation, the calcium in the CaF$_2$ formed on the tooth surfaces is derived from the tooth mineral; i.e., a small amount of the tooth mineral is dissolved with each application, and some of the dissolved calcium is reprecipitated in the form CaF$_2$. In contrast, the inventive compositions, which always contain appropriate amounts of calcium, can supply the calcium needed to form CaF$_2$. Thus, the treatment reaction does not require dissolution of the tooth mineral, and no loss of tooth mineral is expected even with frequent and protracted applications.

More specifically, in accordance with the invention, the rinse or dentifrice is generally formulated in the form of two separate phases (liquids, gels, or pastes) which will be combined just before the application. Phase A contains a soluble calcium salt, and phase B contains a complex fluoride compound. Each phase is stable for indefinite periods in the absence of the other. Shelf stability of a tablet-type product can be enhanced by protecting it from contact with moisture before use. When the two phases are combined, hydrolysis of the complex fluoride will occur which produces sufficient amounts of free fluoride to cause calcium fluoride precipitation. This in turn keeps the free fluoride concentration in the mixture sufficiently low to allow continued hydrolysis of the complex fluoride compound and precipitation of calcium fluoride. With proper concentrations of calcium and complex fluoride in the two solutions, a significant amount of calcium fluoride can be deposited on the tooth surface within a typical application time.

Thus, the present invention includes a method for fluoridating teeth comprising (1) mixing in an aqueous environment a first component comprising a stable, non-toxic soluble calcium salt with a second component comprising a stable, non-toxic readily hydrolyzable complex fluoride compound, resulting in hydrolysis of the fluoride compound and precipitation of calcium fluoride, followed by (2) prompt application of the mixture to tooth surfaces. The invention also contemplates mouth rinses, dentifrices, gels, and chewable tablets for application of the above-described compositions.

In one embodiment, this invention is a method for fluoridating teeth with a reactive, multi-component compound. The method comprises mixing, in an aqueous environment, a first component consisting of a stable, non-toxic soluble calcium salt and a non-reactive carrier, with a second component consisting of a stable, non-toxic readily hydrolyzable complex fluoride compound, and a non-reactive carrier. The first component, the second component, or both the first and second component further include a buffer. The mixture defines a reactive, multi-component composition wherein the complex fluoride compound is hydrolyzed, and calcium fluoride is precipitated from the reactive multi-component compound upon mixing. Next, the reactive, multi-component composition is applied to tooth surfaces.

In a alternative embodiment, the method of this invention comprises mixing, in an aqueous environment, a first component comprising calcium chloride, with a second component comprising sodium fluorosilicate, an acetate salt, and a sufficient quantity of soluble, non-toxic phosphorous salt to maintain the phosphorous concentration of the multi-component compound at no more than about $1 \times 10^{-3}$ mol/L. The mixture defines the reactive, multi-component composition and has a pH of from about 4.5 to about 5.5. The sodium fluorosilicate of the reactive multi-component composition is hydrolyzed upon mixing, and calcium fluoride precipitates from the reactive multi-component composition. Once mixed, the reactive multi-component composition is applied to tooth surfaces for a period of time ranging from about 10 seconds to about 4 minutes.

In another embodiment, this invention is a reactive, multi-component composition consisting of an admixture of a stable, non-toxic soluble calcium salt, a stable, non-toxic readily hydrolyzable complex fluoride compound, a buffer, and one or more non-reactive carriers. The reactive multi-component composition having a useful life of from about 10 seconds to about 4 minutes or longer.

In an alternative embodiment, the reactive multi-component composition comprises calcium chloride, sodium fluorosilicate, about $1 \times 10^{-3}$ mol/L of a non-toxic phosphorous salt, an acetate salt, and one or more non-reactive carriers. The reactive multi-component compound having a pH of from about 4.5 to about 5.5.

DESCRIPTION OF THE PREFERRED EMBODIMENTS

More specifically, the present invention involves a method and materials for fluoridating teeth in situ, in a safe manner simple enough to constitute a regular part of a routine of in-home oral hygiene. The precipitation of fine calcium fluoride particles directly on the tooth surfaces accomplished by the invention is notably advantageous.

The invention contemplates use of a first component comprising a soluble calcium salt as a source of calcium. The salt and the component overall should be non-toxic enough for oral use at the intended levels on a regular basis, and stable for the desired shelf life. Examples of appropriate calcium salts include calcium chloride, calcium acetate, calcium butylate, calcium citrate, calcium lactate, calcium salicylate, and all other non-toxic salts of calcium and inorganic or organic acids which can dissolve in an aqueous solution, preferably to the extent of at least $2 \times 10^{-3}$ mol/L (approximately 0.008 grams of Ca in 100 grams of water).

The soluble calcium component of the two-component system may include a buffer. Examples of such buffers include acetate salts, succinate salts and HEPES. It is preferred that the buffer is an acetate salt. The buffer aids in sustaining the driving force of the fluoride component hydrolysis reaction. The hydrolysis of the preferred fluoride components produce hydrogen ions as well as fluoride ions. The rate of the hydrolysis reaction diminishes as the concentration of hydrogen ions in the solution increases. The addition of a buffer to the two-component system prevents the rapid accumulation of hydrogen ions in the two-component system. This allows the hydrolysis reaction to occur at a steady, high rate thus providing a continuous high level of fluoride ions to the teeth during the time the teeth are exposed to the two-component system.

The invention also contemplates a second component comprising a complex fluoride compound as a source of fluoride. Once again, the complex fluoride compound and the second component overall should be non-toxic enough for oral use at the intended levels on a regular basis, and stable for the desired shelf life. Note that the first and second components may be in contact, as in a chewable tablet, provided that the product is dry and thus will not permit mixing of the components in an aqueous environment leading to hydrolysis of the complex fluoride compound, until water is added. Complex fluoride compounds with hydrolytic properties must be quickly hydrolyzable and are within the scope of the present invention. These compounds include fluorostannate, flourosilicate, fluorozirconate, fluoroborate and fluorophosphate salts. The preferred fluoride compound for purposes of this invention is sodium fluorosilicate ($Na_2SiF_6$). Monofluorophosphate, a fluoride agent used widely in dentifrices, is also generally classified as a complex fluoride, but its hydrolysis is too slow to precipitate a significant amount of calcium fluoride within the typical 1-minute application time. Thus, monofluorophosphate and other slow hydrolyzing complex fluoride compounds such as sodium fluoride are excluded from the invention.

Several factors are known to affect the hydrolysis of sodium fluorosilicate and consequently the effectiveness of fluoride deposition by the two-component rinse. One factor is the pH of the combined solution which decreases with time as hydrogen ions are produced by the hydrolysis. The pH of the rinse can be controlled by using different pH buffers. It is anticipated that if the pH is maintained at a high value above about 4.0, the hydrolysis will proceed quickly. Another factor in the reaction rate is the calcium concentration, which, according to the stoichiometry of the $CaF_2$ precipitation reaction, should ideally be one half of the total F concentration. A higher calcium concentration should increase the rate of $CaF_2$ precipitation. It is preferred that the calcium to fluoride concentration ratio of the reactive multi-component composition ranges from about 0.4 to about 0.6. A third factor is the phosphate concentration. Phosphates may be included in the system to assure that the rinse solution, even at its lowest pH, remains saturated with respect to the tooth mineral so that no loss of tooth mineral would occur. However, a high phosphate concentration can cause precipitation of calcium phosphates which would make less calcium available for $CaF_2$ precipitation. The level of phosphate needed to maintain saturation with respect to tooth mineral depends on the pH and calcium concentration of the rinse solution. In a typical case in which [Ca] is 10 mmol/L, the total [$PO_4$] needed would be $9.4 \times 10^{-8}$, $7.5 \times 10^{-6}$, or $1 \times 10^{-3}$ mol/L at pH 7, 6, or 5, respectively. These [$PO_4$] concentrations correspond to 0.009, 0.071, and 95 ppm of [$PO_4$], respectively. Generally, the phosphorous content of saliva is sufficient to maintain the phosphorous concentration of the rinse at the desired level.

The first component containing the calcium salt and the second component containing the complex fluoride compound are generally mixed in an aqueous environment and promptly applied to the tooth surfaces. The aqueous environment may be the human mouth, or it may be a location outside the human mouth. If a location outside the human mouth is chosen to mix the first and second component, then the reactive multi-component composition should be applied to the teeth within from about 10 seconds to about 4 minutes of mixing. It is preferred that the reactive multi-component composition is applied to the mouth and teeth within about 30 seconds of the initial mixing in an aqueous environment.

The reactive multi-component composition may be contacted with the teeth for a period of time ranging from about 10 seconds to about 4 minutes or longer. However, the composition slowly becomes non-reactive, and after about 4 minutes, depending on solution pH, the composition has lost most of its ability to precipitate fluoride on the teeth and gums.

The pH of the two-component system may vary from about 4.0 to about 7.5. However, it is preferred that the pH of the calcium component of the two-component system ranges from about 4.5 to about 5.5.

The mixing of the reactive multi-component composition may be accomplished in various ways depending on the forms in which the inventive compositions are used. The first and second components of the reactive multi-component composition will typically each contain a non-reactive carrier material. The term non-reactive carrier material is intended to encompass any component of the composition that does not participate in the fluoride precipitation and deposition mechanisms. Examples of such non-reactive carrier materials include liquids, pastes, solids, gels and like materials or mixtures thereof. The non-reactive carrier materials may contain constituents beneficial to teeth or gums which do not react with the first or second components of the composition. Beneficial constituents might include abrasives useful in tooth cleaning, antiseptics, anesthetics, sweeteners to make the composition palatable and other similar beneficial materials. It should be noted that the non-reactive carrier material is not the calcium, fluoride, buffer, or optional phosphorous composition of the first and second components of the multi-component composition.

Examples of forms the reactive multi-component composition might take include:

(1) For fluoride rinses, the two solutions may be contained in separate compartments in a receptacle or container or in separate receptacles or containers. Measured amounts of the two solutions are then delivered to a third compartment, preferably near the opening of a single multi-compartment receptacle (similar to the bottles used for the ACT$^R$ brand fluoride rinse). Mixing will occur as the solutions are combined in this compartment, and when the solution is swished in the mouth. The combined solution should be used within a reasonable period of time, e.g., 30 seconds, after mixing.

(2) For fluoride dentifrices, the two pastes containing the two components may be held in separate compartments in a tube or tubes similar to those used for dentifrices. Measured amounts of the two pastes will then be extruded from the tube(s) onto a tooth brush. The mixing of the two components, i.e., soluble calcium and complex fluoride, will occur as the brushing begins.

(3) For professionally applied topical fluoride gels, either of the above two forms of packaging or an alternate form of packaging may be used depending on the consistency of the gel considered most desirable. Generally, measured amounts of the two gels are dispensed from the container and mixed by stirring or spatulation. The combined gel is then placed in a tray and the tray is held tightly against the upper or lower arch of teeth for a desired period, e.g., 4 minutes.

(4) For chewable tablets, mixing will occur upon chewing and dissolution of the components in the mouth.

The basic system described above can be modified to improve its effectiveness and safety for frequent use as follows:

(1) Phase B (the fluoride phase) may also contain some phosphate so that when phases A (the calcium phase) and B are combined, the solution is always supersaturated with respect to the tooth mineral to assure that no dissolution of the tooth can occur even with frequent applications.

(2) Since hydrolysis of the complex fluoride produces free fluoride as well as hydrogen ions, to maintain the pH of the dentifrice or rinse constant above approximately 5, pH buffer may be added to either phase A and/or B.

Given below are the compositions of two formulations, one for rinses and the other for dentifrices, which have been tested.

EXAMPLE I

Fluoride Rinses: A typical rinse formulation used in our study consists of (1) solution A which is 20 mmol/L in $CaCl_2$ and 10 mmol in sodium acetate, and (2) solution B which is 4 mmol/L in $Na_2SiF_6$, and 5 mmol/L each in $Na_2HPO_4$ and $NaH_2PO_4$. Alternatively, sodium fluorostannate may be used as the complex fluoride in this formulation. When equal volumes of A and B are mixed, the total fluoride concentration is 228 ppm, which is slightly lower than the fluoride concentrations in most fluoride rinses in use today. The hydrolysis of $SiF_6^{2-} SiF_6^{2-} + 2H_2O \rightarrow SiO_2 + 6F^- + 4H^+$, is controlled by both the $F^-$ and $H^+$ concentrations in the solution. Thus, the hydrolysis does not occur appreciably in solution B because of accumulation of free $F^-$ ions, but in the combined solution the precipitation of calcium fluoride removes free $F^-$ and allows the hydrolysis to proceed. This in turn allows calcium fluoride precipitation to continue. The acetate buffer consumes most of the $H^+$ ions produced by the hydrolysis reaction so that the pH remains above 5. The phosphate present in the system assures that the solution is always supersaturated with respect to hydroxyapatite and fluorapatite so that no loss of tooth mineral occurs even with frequent applications. The above rinse is preferably used by combining 5 ml each of solutions A and B and rinsing for about 1 minute.

EXAMPLE II

Fluoride Dentifrices: Dentifrices are chemically more complex than the rinses because they contain among other things abrasive particles, detergents, and nonaqueous liquids. However, the basic principle for precipitating calcium fluoride from a 2-component system described above for the rinses can also be applied to dentifrices.

For the dentifrice formulation, the total fluoride content is higher (1000 ppm in currently used dentifrices), but the recommended quantity per application is lower (1 gram for dentifrices versus 10 mL for rinses). A typical dentifrice formulation used in our study consists of (1) paste A which contains 100 grams of a fluoride free paste with methylmethacrylate particles as the abrasives, to which 0.89 grams of $CaCl_2$ and 0.33 grams of sodium acetate are added, and (2) paste B which contains 100 grams of the same fluoride free paste to which 0.30 grams of $Na_2SiF_6$, 0.014 grams of $NaH_2PO_4 \cdot H_2O$, and 0.027 grams of $Na_2HPO_4 \cdot 7H_2O$ are added. In order for paste B to be stable for long periods, it should not contain soluble calcium compounds or calcium containing abrasive particles. Also, results from recent studies show that the inorganic abrasive particles, such as hydrated silica in Pepsodent ®, tend to induce $CaF_2$ precipitation to occur onto the surfaces of the abrasives. This causes a reduction of fluoride deposition on tooth surfaces. Currently, we were able to obtain more reproducible results using methylmethacrylate.

When equal amounts of pastes A and B are combined, the total fluoride content is 909 ppm, less than that of most of the fluoride dentifrices presently used, and the concentrations of other components are $[CaCl_2] = 40$ mmol/L, $[NaH_2PO_4 \cdot H_2O] = 0.5$ mmol/L, $[Na_2HPO_4 \cdot 7H_2O] = 0.5$ mmol/L, and [Na Acetate] = 20 mmol/L. The above dentifrice is preferably used by combining 0.5 grams each of pastes A and B and brushing for about 1 minute.

The CCT technique was used to measure the fluoride deposited on tooth surfaces by the above new formulations. The results show that 5.5 and 2.2 micro grams/cm$^2$ of fluoride were deposited by the dentifrice and rinse, respectively. These values are approximately 16 and 9 times higher than the fluoride deposition from the currently used fluoride dentifrices and rinses, respectively, even though the total amounts of fluoride contained in the above rinse and dentifrice formulations are 228 and 909 ppm, respectively, which are lower than those in the fluoride rinses and dentifrices currently in use. Thus, these new formulations are likely to be significantly more effective.

The amounts of fluoride deposited on tooth surfaces by the various experimental and commercial formulations are summarized in Table 1.

TABLE 1

Amount of Fluoride Deposition on Tooth Surfaces Produced by 1-minute Application with the Various Formulations

| Treatment | Fluoride Content in ppm | Fluoride Deposited on Tooth Surfaces micro grams/cm$^2$ |
|---|---|---|
| ACT ® Fluoride Rinse | 250 | 0.34 ± 0.10 |
| Calcium Fluoride Slurry | 250 | 0.28 ± 0.05 |
| Ammonium Fluoride Soln | 250 | 0.30 ± 0.05 |
| Inventive fluoride Rinse | 230 | 5.50 ± 0.32 |
| Crest ® Toothpaste | 1000 | 0.25 ± 0.23 |
| Colgate ® Toothpaste | 1000 | 0.04 ± 0.03 |
| Inventive fluoride Toothpaste | 910 | 2.20 ± 0.21 |

EXAMPLE III

Chewable fluoride supplement tablets can be formulated in a similar way. Since the tablets are packaged in a water free state, the two components described above can be safely included in same tablet; the reaction between the calcium and complex fluoride will begin after they are in contact with the saliva by virtue of the chewing action.

Other topical fluoride regimens that are being used clinically at present include: (1) mouth rinses containing 900 ppm or more of fluoride for weekly use, (2) 0.4% stannous fluoride ($SnF_2$) gels, equivalent to 970 ppm in fluoride, for daily self-applications, and (3) acidulated phosphate fluoride (APF) gels, with 1.23% fluoride, 1% $H_3PO_4$, pH 3 to 3.5, for professional tray application use.

EXAMPLE IV

A Fluoride Rinse for Weekly Use

This system consists of (1) solution A, which is 80 mmol/L in $CaCl_2$ and 40 mmol/L in sodium acetate, and (2) solution B, which is 16 mmol/L in $Na_2SiF_6$, and 20 mmol/L each in $Na_2HPO_4$ and $NaH_2PO_4$. Alternatively, calcium acetate or calcium lactate may be used as the calcium source in this formulation. Coloring and flavoring agents are also added to one or both solutions to suit consumer preferences. When equal volumes of A and B are mixed, the total fluoride concentration is 912 ppm, which is about the same as that in the fluoride rinses formulated for weekly use. The chemical reactions which will occur are basically the same as those given in EXAMPLE I, except that the concentrations of all reactants are higher. It is anticipated that the reactions will proceed rapidly and most of the fluoride in the rinse will precipitate out during the one minute application time. The above rinse is preferably used by combining 5 mL each of solutions A and B and rinsing for one minute.

EXAMPLE V

A Stannous (Tin [II]) and Fluoride Containing Gel for Self-Application

The system consists of two gels: (1) gel A is 80 mmol/L in $CaCl_2$ and 40 mmol/L in sodium acetate in water, and (2) gel B is 51 mmol/L in $SnCl_2$ and 17 mmol/L in $Na_2SiF_6$ in glycerine. ($SnF_2$ gels are usually formulated in 98% glycerine to maintain the stability of $SnF_2$.) Thickening, coloring and flavoring agents are added to one or both gels to obtain the desired consistency, and to suit consumer preferences. When equal volumes of gels A and B are combined, the tin concentration is 0.30 wt %, and the total fluoride concentration is 970 ppm. These concentrations are approximately the same as those in the 0.5 wt % $SnF_2$ gels currently in use. Thus, it may be anticipated that the inventive formulation would have approximately the same antiplaque effects as those attributable to $SnF_2$ at the same concentration. Unlike the $SnF_2$ gels, however, the inventive gel will allow the calcium fluoride to rapidly precipitate onto the surface of the teeth within the one minute application time. The above gel is preferably used by placing equal volumes of gels A and B on a tooth brush and working the gels over the surface of the teeth. After one minute, expectorate, but do not rinse.

EXAMPLE VI

An Acidic Phosphate Fluoride Gel for Professional Tray Application Use

This gel, which is intended to be used in the same way as the acidulated phosphate fluoride (APF) gel, consists of two gels: (1) gel one is 0.3 mol/L in $CaCl_2$ and 0.15 mol/L in sodium acetate in water, and (2) gel B is 0.2 mol/L in $H_2SiF_6$ (we use the acid here because the sodium and other salts are not sufficiently soluble to prepare a 0.2 mol/L solution), and 0.1 mol/L each in $(NH_4)_2HPO_4$ and $(NH_4)H_2PO_4$ in water. Thickening, coloring and flavoring agents are also added to one or both gels to obtain the desired consistency, and to suit consumer preferences. When equal amounts of the two gels are combined, the total fluoride concentration is 1.14% and the $H_3PO_4$ concentration is 0.098%; these are about the same as those in the currently used APF gels. As in all other inventive formulations, hydrolysis of $SiF_6^{2-}$ ions would produce free fluoride ions which then react with the $Ca^{2+}$ ions in the formulation to cause calcium fluoride to precipitate rapidly without dissolving any significant amount of tooth mineral. The above gel is preferably used by placing equal amounts of gels A and B in a tray and applying the mixture to the surface of the teeth for four minutes.

EXAMPLE VII

Effects of Calcium and Phosphate Concentrations and pH Buffer on Fluoride Deposition From Two-Component Rinse System Containing Sodium Fluorosilicate In order to determine the optimum conditions for maximum F deposition at a given $Na_2SiF_6$ concentration, we have conducted a study in which the [F], [Ca], and [PO$_4$] concentration parameters were varied as follows.

1. The pH of the rinse were controlled by using different pH buffers:
   Acetate—pH range 4.5 to 5
   Succinate—pH range 5.5 to 6
   HEPES—pH range 7 to 7.5
2. The calcium concentrations varied from 2 to 50 mmol/L in the combined rinse solution.
3. The phosphate concentrations varied from 1 to 25 mmol/L in the combined rinse solution. The F deposition was measured by the constant composition titration technique described previously. In addition, for each rinse tested the pH of the rinse was measured at 1 minute after mixing the two solutions. This particular time was chosen because it corresponds to the approximate time when the rinse application would be finished. The results are outlined below.

A. Two-component Rinse Solutions Containing Acetate Buffer

Each rinse was prepared by mixing equal volumes of a solution selected from the E series and one selected from F series. The compositions of the solutions are given in Table II and the amounts of F deposition are listed in Table III.

TABLE II

Composition of Two-component Rinse Solutions Containing Acetate Buffer.

| Soln | [CaCl$_2$] | [Na Acetate] | [Na$_2$SiF$_6$] | [NaH$_2$PO$_4$] | [Na$_2$HPO$_4$] |
|---|---|---|---|---|---|
| E1 | 4 mmol/L | 50 mmol/L | — | — | — |
| E2 | 20 | 50 | — | — | — |
| E3 | 100 | 50 | — | — | — |
| F1 | — | — | 4 mmol/L | 1 mmol/L | 1 mmol/L |
| F2 | — | — | 4 | 5 | 5 |
| F3 | — | — | 4 | 25 | 25 |

TABLE III

Mean ± S.D. (n = 3) of Fluoride Deposition (micro grams of F deposited per cm$^2$ of enamel surface) by Two-component Rinses containing Acetate Buffer. Numbers in () Denote pH of the Rinse at One Minute after Mixing of the Two Solutions.

| | Na$_2$SiF$_6$ and P Containing Solutions | | |
|---|---|---|---|
| Ca Soln | F1 | F2 | F3 |
| E1 | 1.22 ± 0.04 | 1.47 ± 0.38 | 0.36 ± 0.08 |
| | (5.02) | (5.16) | (6.29) |
| E2 | 5.41 ± 0.21 | 3.30 ± 0.20 | 0.41 ± 0.02 |
| | (4.99) | (5.05) | (5.98) |
| E3 | 2.43 ± 0.38 | 0.34 ± 0.03 | 0.19 ± 0.07 |
| | (4.76) | (4.77) | (5.26) |

B. Two-component Rinse Solutions Containing Succinate Buffer

Each rinse was prepared by mixing equal volumes of a solution selected from the C series and one selected from F series. The compositions of the solutions are given in Table IV and the amounts of F deposition are listed in Table V.

TABLE IV

Composition of Two-component Rinse Solutions containing Succinate Buffer.

| Soln | [CaCl$_2$] | [NaSuccinate] | [Na$_2$SiF$_6$] | [NaH$_2$PO$_4$] | [Na$_2$HPO$_4$] |
|---|---|---|---|---|---|
| C1 | 4 mmol/L | 50 mmol/L | — | — | — |
| C2 | 20 | 50 | — | — | — |
| C3 | 100 | 50 | — | — | — |
| F1 | — | — | 4 mmol/L | 1 mmol/L | 1 mmol/L |
| F2 | — | — | 4 | 5 | 5 |
| F3 | — | — | 4 | 25 | 25 |

TABLE V

Mean ± S.D. (n = 3) of Fluoride Deposition (micro grams of F deposited per cm$^2$ of enamel surface) by Two-component Rinses containing Succinate Buffer. Numbers in () Denote pH of the Rinse at One Minute after Mixing of the Two Solutions.

| | Na$_2$SiF$_6$ and P Containing Solutions | | |
|---|---|---|---|
| Ca Soln | F1 | F2 | F3 |
| C1 | 0.48 ± 0.18 | 0.52 ± 0.14 | 0.16 ± 0.05 |
| | (5.63) | (5.92) | (6.56) |
| C2 | 3.07 ± 0.16 | 1.98 ± 0.47 | 0.35 ± 0.10 |
| | (5.55) | (5.62) | (6.30) |
| C3 | 0.55 ± 0.15 | 0.24 ± 0.08 | 0.25 ± 0.03 |
| | (5.27) | (5.2) | (5.58) |

C. HEPES containing rinses produced very low F deposition; the highest value was less than 1 micro gram/cm$^2$.

The following conclusions may be drawn from the above results:

(1) Effects of calcium concentration—There is an optimum [Ca], probably close to the stoichiometric amounts of calcium needed for CaF$_2$ precipitation. A low [Ca] decreased the F deposition because of insufficient Ca for precipitating out all the F as CaF$_2$; A high [Ca] also decreased F deposition.

(2) Effects of phosphate concentration—Phosphate has a strong negative effect on F deposition; it sharply decreases the F deposition. This trend is clearly seen in three of the six series (C2, E2, and E3) shown in Tables III and V above. In two series (E1 and C1), phosphate effects were insignificant in the rinses containing lower levels of phosphate, i.e., 1 and 5 mmol/L. But F deposition was insignificantly lower in the rinse containing 25 mmol/L phosphate. In series C3, the effect of phosphate is unclear because of the very low F deposition at all three [P] tested.

(3) Effects of pH buffer—Among the three pH buffers used, acetate which has a pK$_a$ of 4.75 (the pH at which it has the maximum buffer capacity), produced the highest amount of F deposition. Succinate, with two pK$_a$'s at 4.16 and 5.61 (5.61 is the relevant pK here because the disodium salt was used), produced less F deposition. HEPES with pK$_a$ of 7 produced the least F deposition. The reason for this appears to be that when the solution pH was high the SiF$_6^{2-}$ hydrolysis and CaF$_2$ precipitation occur rapidly. These reactions were essentially over before the rinse solution was brought in contact with the tooth.

D. In another experiment we compared F deposition by three rinse solutions all of which had [Ca]=10 mmol/L, [P]=5 mmol/L, and [Na$_2$SiF$_6$]=4 mmol/L, but with [NaAcetate]=5, 12.5 or 25 mmol/L in the combined solution. The F deposition from the three rinses were 1.29±0.16, 2.09±0.12, and 5.41±0.21 micro grams/cm$^2$, respectively. The pH of the three rinses measured at 1 minute after mixing were 3.89, 4.48, and 4.99 micro grams/cm$^2$ respectively. These results clearly show that when the pH gets too low (because of low acetate concentrations) the F deposition sharply because hydrolysis is slower at lower pH's.

In summary, for maximum effectiveness, there is an optimum [Ca], a specific range of pH as controlled by appropriate buffer, and a minimum [P] only to maintain saturation with respect to tooth mineral. The optimum conditions listed above were determined for rinses using $Na_2SiF_6$ as the source of F, and at a total F concentration of 228 ppm (12 mmol/L). The optimum F concentration will vary for rinse, gel or tablet formulations, and they will need to be determined experimentally. However, the principles that govern the effects of Ca, P and pH buffer would remain the same.

E. Two-component Rinse Solutions containing Acetate Buffer

Each rinse was prepared by mixing equal volumes of a solution selected from the E series and one selected from F series. The compositions of the solutions are given in Table VI and the amounts of F deposition are listed in Table VII.

TABLE VI

Composition of Two-component Rinse Solutions containing Acetate Buffer. Soln

| | [CaCl$_2$] | [NaAcetate] | [Na$_2$SiF$_6$] | [NaH$_2$PO$_4$] | [Na$_2$HPO$_4$] |
|---|---|---|---|---|---|
| E1 | 4 mmol/L | 25 mmol/L | — | — | — |
| E2 | 20 | 25 | — | — | — |
| E3 | 100 | 25 | — | — | — |
| F1 | — | — | 4 mmol/L | 1 mmol/L | 1 mmol/L |
| F2 | — | — | 4 | 5 | 5 |
| F3 | — | — | 4 | 25 | 25 |

TABLE VII

Mean (n = 3) Fluoride Deposition (micro grams of F deposited per cm$^2$ of enamel surface) by Two-component Rinses containing Acetate Buffer. Numbers in () Denote pH of the Rinse at One Minute after Mixing of the Two Solutions.

| | Na$_2$SiF$_6$ and P Containing Solutions | | |
|---|---|---|---|
| Ca Soln | F1 | F2 | F3 |
| E1 | 1.42 ± 0.17 (4.67) | 2.04 ± 0.12 (4.83) | 0.88 ± 0.33 (6.30) |
| E2 | 2.09 ± 0.12 (4.48) | 4.36 ± 0.17 (4.67) | 1.12 ± 0.13 (5.98) |
| E3 | 3.19 ± 0.29 (4.20) | 0.92 ± 0.07 (4.24) | 0.33 ± 0.07 (5.14) |

The fluoride deposition values, found in Table VII for the solutions shown in Table VI are lower than the fluoride deposition values found in Table V for the solutions shown in Table IV. The only difference between the solutions shown in Tables IV and VI are the sodium acetate concentrations. The solutions of Table IV having a sodium acetate concentration of 50 mmol/L exhibited a greater ability to deposit fluoride on enamel than did the solutions of Table VI having an acetate concentration of 25 mmol/L. The solutions having the higher sodium acetate concentrations also have a higher pH one minute after mixing, which in turn results in improved fluoride deposition values.

It should be understood that the foregoing disclosure emphasizes certain specific embodiments of the invention and that all modifications or alternatives equivalent thereto are within the spirit or scope of the invention as set forth in the appended claims.

What is claimed is:

1. A method for fluoridating teeth with a reactive, multi-component composition comprising:
   (a) mixing in an aqueous environment, a first component comprising calcium chloride, with a second component comprising sodium fluorosilicate, an acetate salt, and a sufficient quantity of soluble, non-toxic phosphorous salt to maintain the phosphorous concentration of the multi-component compound at no more than about $1 \times 10^{-3}$ mol/L the mixture defining a reactive, multi-component composition having a pH of from about 4.5 to about 5.5, wherein the sodium fluorosilicate of the reactive multi-component composition is hydrolyzed, and calcium fluoride is precipitated from the reactive multi-component composition; and
   (b) applying the reactive multi-component composition to tooth surfaces for a period of time ranging from about 10 seconds to about 4 minutes.

2. A method as in claim 1 wherein the mixture is applied to tooth surfaces within about thirty seconds of mixing.

3. A method as in claim 1 wherein the soluble, non-toxic phosphorous salt is selected from the group consisting of alkali and alkaline phosphorous salts, ammonium salts of phosphorous, salts of orthophosphoric acid or mixtures thereof.

4. A method as in claim 3 wherein the water soluble, non-toxic salt phosphorous is selected from the group sodium hydrogen phosphate, sodium dihydrogen phosphate, or mixtures thereof.

5. A method as in claim 1 wherein the aqueous environment is the human mouth.

6. A method as in claim 1 wherein the aqueous environment is supplied by the first component, by the second component, or by both the first and second component.

7. A method as in claim 1 wherein the first component and the second component may be in the form of a paste a gel, an aqueous solution, or a combination thereof.

* * * * *